United States Patent [19]
Puricelli

[11] Patent Number: 4,910,222
[45] Date of Patent: Mar. 20, 1990

[54] CYSTEINE DERIVATIVES HAVING EXPECTORANT ACTIVITY

[75] Inventor: Laura Puricelli, Brescia, Italy

[73] Assignee: Magis Farmaceutici SpA, Italy

[21] Appl. No.: 225,769

[22] Filed: Jul. 29, 1988

[30] Foreign Application Priority Data

Jul. 30, 1987 [IT] Italy ................................ 21514 A/87

[51] Int. Cl.⁴ ................ A61K 31/265; C07C 153/017; C07C 153/023
[52] U.S. Cl. ..................................... 514/513; 558/254
[58] Field of Search ........................ 558/254; 514/513

[56] References Cited

U.S. PATENT DOCUMENTS 2,406,362  8/1946  Farlow ................................. 558/254

Primary Examiner—Mary C. Lee
Assistant Examiner—Robert C. Whittenbaugh
Attorney, Agent, or Firm—Arnold, White & Durkee

[57] ABSTRACT

The present invention covers D or L or DL-cysteine derivatives of the general formula (I)

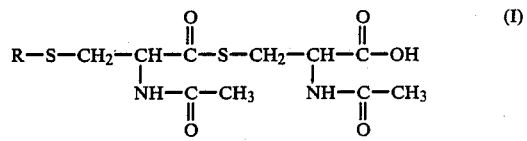

wherein R represents H or a fatty saturated or unsaturated acid radical, or a radical of an aromatic acid such as benzoic, cynnamic, salycilic, 2-acetoxybenzoic acid or a heterocyclic acid, as well as their salts, in particular the Ca and Mg salts.

The invention refers also to a process for preparing said derivatives and to the pharmaceutical preparations containing them as active principle, having a bronchial liquefying and expectorating activity.

8 Claims, No Drawings

CYSTEINE DERIVATIVES HAVING EXPECTORANT ACTIVITY

The present invention refers to new cysteine derivatives of the general formula (I)

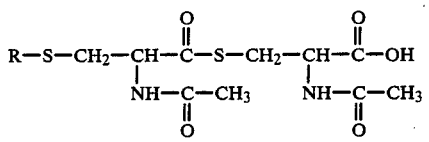

in which R represents a radical of a fatty saturated or unsaturated acid, or a radical of an aromatic acid, such as benzoic, salicylic, cynnamic, 2-acetoxy-benzoic acid or of a heterocyclic acid, as well as their salts, particularly Ca and Mg salts.

The new derivatives are excellent bronchial liquefiers and expectorants,

INVENTION FIELD

The invention refers to new cysteine derivatives having a bronchial liquefying and expectorant activity, to a process for their preparation and to pharmaceutical compositions containing them as active ingredients.

DESCRIPTION

Operating according to the above mentioned reaction series, the starting compound for the preparation of derivatives of formula (I) according to the invention is the chloride of 3-chloro-L-alanine(II) which may be obtained from 3-chloro-1-alanine by any of the conventional methods employed for transforming an acid into its chloride, for instance by reaction with phosphorus pentachloride in a suitable solvent, such as chloroform or diethyl ether.

The chloride is obtained as a precipitate from the reaction mixture by addition of e.g. ligroin (in the ether solutions) or of diethyl ether (in the chloroform solutions). The filtered product is reacted with an excess of potassium hydrosulfide (III) to obtain the L-2-ammino thiopropionic acid (IV).

Compound (IV) is acetylated to obtain (VI) by any of the conventional methods employed for acylating an amino group, e.g. by reaction with acetyl chloride in a suitable solvent, such as chloroform, in the presence of an acid acceptor.

Derivative (VI) by reaction in an alkaline medium with a thio-acid (VII) provides compound (VIII), which by reaction in an alkaline medium with derivative (IX) provides derivative (I). The reaction between compound (VIII) and compound (IX) is carried out at a pH between 5 and 7 and at a temperature between 15° and 25° C. Derivative (I) is obtained in a state of high purity by purification on a silica gel column, using as eluent chloroform-methanol (7:3).

Operating according to (b) above, an alkali salt of acetyl-3-chloroalanine (X) is reacted with ethyl chloroformate (XI) and the mixed anhydride obtained (XII) as reacted with L-acetyl-cysteine (XIII) to give derivative (XIV); finally (XIV) by reaction in alkaline medium with the thioacid (VII), gives (I) which is purified on a silica gel column, employing as a eluent a chloroform-methanol 7:3 mixture.

The reaction between compound (XII) and compound (XIII) is carried out at a pH between 6 and 8 and at a temperature of between −23° and −17° C., while the reaction between compound (XIV) and (VII) is carried out at a pH between 5 and 7 and at a temperature of between 15° and 25° C.

The present invention also comprises pharmaceutical compositions containing as active ingredients one or more of the compounds of the invention, together with parmaceutically acceptable vehicles and diluents.

The pharmaceutical compositions may be in the following forms:

solid, such as capsules, tablets or bonbons with instantaneous or retarded action, monodosis sachets; liquid, such as solutions or emulsions instantaneous or retarded; as suppositories; solutions for injection or for instantaneous or delayed inhalation.

In the treatment of bronchial affections, the compounds according to the invention may be administered orally in posologic doses containing, e.g., between 100 and 5000 mg of active substance two, three or four times a day; by injection and inhalation in posologic units of between 50 and 500 mg of active substance, two, three or four times a day; rectally in posologic units of 100 to 1000 mg of active substance two, three or four times a day.

The derivatives of the invention are good bronchial liquefiers and expectorants, superior to cysteine at equal doses, while showing low toxicity.

The $DL_{50}$ value determined on mice and rats, both intraperitoneally and orally, is higher than 3000 mg/Kg for all the examined compounds. The expectorant activity ($DE_{50}$), determined on rabbits according to (Boyd and Sheppard, Arch. Int. Pharm, 1966, 163, 284, is 100 mg/Kg. The same $DE_{50}$ determined on mice according to a modified Mavatari method shown in (Graziani, Cazzulani, Il Farmaco Ed. Prat. 1981 XXXVI, 3, 167, is respectively of 37 mg/Kg.

The following examples will illustrate the process of the invention without limiting it.

EXAMPLE 1

Preparation of N-acetyl-S-{N-acetyl[(benzoyl)thio]alanyl}cysteine

1. Preparation of L-3-chloro-2-acetamido-thiopropanoic acid:

In a 200 ml flask a solution is prepared by stirring 20 g (0.3 mol) of potassium hydroxide in 80 ml 90% ethanol.

Into the flask a 50 ml separatory funnel is inserted and provided with a tube through which hydrogen sulphide is introduced until the solution is saturated and no longer alkaline to phenotphthalein.

The mixture is cooled on ice to 10°–15° C. and 0.3 mol (49.3 g) of 3 chloro-L-alanine chloride-hydrochloride are added in 90 minutes while stirring at a temperature of 15° C.; the reaction mixture is then stirred for an additional hour.

The potassium chloride which is formed is filtered off, washed with 20 ml 95% ethanol, the solutions are put together and ethanol is evaporated under reduced pressure.

The solid residue is dissolved in 70 ml of cold water and the solution is filtered.

0.3 mol acetyl chloride are then added slowly, under strong stirring and under control of the pH, which should be about 8.

The solution is stirred for an additional hour and acidified to pH 2.0 with hydrochloric acid.

The formed precipitate is filtered off, washed with water and dried in a oven. The dry product is crystallized from water.

15 g of product are obtained.

The structure is confirmed by spectral analysis.

| Elemental Analysis: | C | H | Cl | N | S |
|---|---|---|---|---|---|
| Calculated Amount: | 33.06% | 4.43% | 19.50% | 7.71% | 17.65% |
| Amount Found: | 33.5% | 4.5% | 19.3% | 7.7% | 17.5% |

2. Preparation of L-3-benzoyl mercapto-2-acetamido thiopropanoic acid:

54.3 g (0.3 mol) of L-3-chloro-2-acetamido-thiopropanoic acid are suspended in 150 ml of water brought to pH 5.0 by addition of sodium hydroxyde. The temperature is brought to 20° C. and 46 g thiobenzoic acid, 24 g anydrous potassium carbonate and 300 ml water are added rapidly. A yellow, almost clear solution is obtained at pH 6.06 which is left standing overnight (in the darkness) at about 18° C.

Thereafter 21 mol 35% hydrochloric acid are added slowly under pH control until a stable pH of 4.0 is reached.

The formed precipitate is filtered on a Büchner funnel and washed with 4×100 ml water.

The product is then oven dried.

Approximately 80 g of product are obtained. The structure is confirmed by spectral analyses.

| 51.14% | 5.07% | 5.42% | 24.85% |
|---|---|---|---|
| 51.2% | 5.04% | 5.44% | 24.7% |

3. Preparation of N-acetyl-S-{N-acetyl[(benzoyl)thio]alanyl}cysteine:

49.69 g (0.3 mol) 3-chloro-N-acetyl-alanine are suspended in 150 ml of water, which is then brought of pH 5.0 by adding sodium hydroxide. The temperature is brought to 20° C. and 78.5 g of L-3-benzoyl mercapto-2-acetamido-thiopropanoic acid, 24 g anhydrus potassium carbonate and 300 ml water are rapidly added.

A yellow almost clear solution is obtained at a pH of 6.06 which is left standing for one night at 18° C., in the darkness.

Thereafter 35% hydrochloric acid is added slowly, under pH control, to a stable pH to 4.0.

The precipitate is filtered off, washed with 4×100 ml water and oven dried. 120 g of product are obtained which can be purified by dissolving it in ethyl acetate and reprecipitating it by addition of ligroin or ethyl ether.

The structure is confirmed by spectral analysis.

| 51.36% | 5.277% | 7.046% | 16.13% |
|---|---|---|---|
| 51.4% | 5.28% | 7.1% | 16.2% |

EXAMPLE 2

Preparation of N-acetyl-s-(N-acetyl alanyl)cysteine:

1. Preparation of N-acetyl-s-(N-acetyl-3-chloro-alanyl) cysteine

Suspension A

In a 4 neck, 2 liter flask provided with stirrer, thermometer, calcium chloride protection tube, 67.20 g (0.330 mol) of finely powdered potassium salt of N-acetyl-3-chloro-L-alanine and 600 ml acetone are introduced. After cooling to 20° C., 33.6 g ethyl chloroformate and 26 mol N-methyl morpholine are added. The suspension is left standing for two hours at a temperature of 10° C. or lower, and then brought to 30° C.

Solution B 50 g (0,276 mol) of N-acetyl-cysteine, 70 ml acetone and 25 g triethylamine are placed into a 400 ml beaker while stirring and under pH control in such a way that the pH does not rise above 7.5.

The solution is then cooled to 0° to −3° C.

Reaction

Solution B is added to suspension A under stirring within a few minutes keeping the temperature at −15° to −20° C.

The turbid solution is kept at −15° to −20° C. for three hours under stirring, then the temperature is raised to 0° C. and the stirring is continued for an additional 4 hours.

170 ml of water are then added and the solution is placed into a 2 liter beaker. It has a pH of aproximately 6.25.

Keeping the temperature at between 0° and 5° C., hydrochloric acid is added to a constant pH of 4.0.

The solution is extracted with 1000 ml methylene chloride.

The precipitate which is formed is filtered off and washed with 4×100 ml of water. It is then dried in an oven obtaining 70 g of product.

The structure is confirmed by spectral analysis.

| 38.09% | 5.656% | 9.871% | 11.299% | 12.495% |
|---|---|---|---|---|
| 38.2% | 5.66% | 9.88% | 11.25% | 12.4% |

2. (Preparation of N-acetyl-s-(N-acetyl-alanyl)cysteine

In a 200 ml flask a solution of 20 g (0.3 mol) of potassium hydroxide in 80 ml 90% ethanol is prepared. Into the flask a 50 ml separatory funnel is inserted and provided with a tube through which hydrogen sulphide is introduced until the solution is saturated and no longer alkaline to phenophthalein.

The mixture is cooled on ice to 10°–15° C. and 0.3 mol (85.12 g) of N-acetyl-s-(N-acetyl-3-chloro alanyl) cysteine are added.

The mixture is heated on reflux for two hours.

After cooling and filtration, the filtrate is diluted with 100 ml water.

The pH is brought to 4.0. The obtained precipitate is filtered off, washed with water and oven dried.

Aproximately 75 g of product are obtained.

The structure is confirmed by instrumental analysis

| 38.95% | 5.198% | 9.083% | 20.79% |
|---|---|---|---|
| 38.9% | 5.2% | 9.1% | 20.2% |

EXAMPLE 3

Preparation of N-acetyl-s-{N-acetyl[(benzoyl)thio]alanyl}cysteine

Thiobenzoic acid is reacted with N-acetyl-s-(N-acetyl-3-chloroalanyl)cysteine

EXAMPLE 4

The derivatives obtained in the preceding examples are treated with Ca(OH)$_2$ to obtain the respective salts.

I claim:

1. A cysteine compound of the formula:

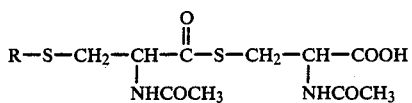

wherein R is H or an acid functional group selected from the group consisting of: benzoic acid, cynnamic acid, salicylic acid, 2-acetoxy benzoic acid, or a therapeutically active salt thereof.

2. A therapeutically active Ca or Mg salt of a compound according to claim 1.

3. A pharmaceutical composition, administrable by injection, by aerosol, or orally or rectally, having expectorant and liquefying bronchial action, comprising an effective amount of a cysteine compound according to claim 1.

4. N-acetyl-s-(N-acetyl-thio-alanyl)cysteine.

5. N-acetyl-s-{N-acetyl-3-[(benzoyl)thio]alanyl}cysteine.

6. N-acetyl-s-{N-acetyl-3-[(2-acetoxibenzoyl)thio]alanyl}cysteine.

7. N-acetyl-S-{N-acetyl-3-[(cynnamoyl)thio]alanyl}cysteine.

8. N-acetyl-S-{N-acetyl-3-[(2-oxybenzoyl)thio]alanyl}cysteine.

* * * * *